United States Patent
Hutchings et al.

(10) Patent No.: US 11,077,102 B2
(45) Date of Patent: Aug. 3, 2021

(54) MULTIDOSE PACKAGE, COURSE AND METHOD OF TREATMENT FOR DELIVERING PREDETERMINED MULTIPLE DOSES OF A PHARMACEUTICAL

(71) Applicant: BAUSCH HEALTH IRELAND LIMITED, Dublin (IE)

(72) Inventors: Mark J. Hutchings, Thornleigh (AU); Christiaan M. Niekerk, Thornleigh (AU)

(73) Assignee: BAUSCH HEALTH IRELAND LIMITED, Dublin (IE)

( * ) Notice: Subject to any disclaimer, the term of this patent is extended or adjusted under 35 U.S.C. 154(b) by 0 days.

(21) Appl. No.: 16/280,600

(22) Filed: Feb. 20, 2019

(65) Prior Publication Data

US 2019/0350924 A1    Nov. 21, 2019

Related U.S. Application Data

(60) Continuation of application No. 14/629,176, filed on Feb. 23, 2015, now abandoned, which is a division of application No. 13/262,782, filed as application No. PCT/AU2010/000372 on Apr. 1, 2010, now Pat. No. 8,962,649.

(30) Foreign Application Priority Data

Apr. 1, 2009    (AU) .................... 2009901410

(51) Int. Cl.

| A61K 31/4745 | (2006.01) |
| A61P 17/02 | (2006.01) |
| A61P 15/00 | (2006.01) |
| A61P 17/00 | (2006.01) |
| A61K 9/00 | (2006.01) |
| A61K 9/06 | (2006.01) |
| A61K 31/437 | (2006.01) |
| A61J 1/00 | (2006.01) |
| B65B 3/04 | (2006.01) |

(52) U.S. Cl.
CPC ............. *A61K 31/4745* (2013.01); *A61J 1/00* (2013.01); *A61K 9/0014* (2013.01); *A61K 9/06* (2013.01); *A61K 31/437* (2013.01); *A61P 15/00* (2018.01); *A61P 17/00* (2018.01); *A61P 17/02* (2018.01); *B65B 3/04* (2013.01)

(58) Field of Classification Search
None
See application file for complete search history.

(56) References Cited

U.S. PATENT DOCUMENTS

| 5,238,944 | A | 8/1993 | Wick et al. |
| 6,821,523 | B2 | 11/2004 | Maibach et al. |
| 6,894,060 | B2 | 5/2005 | Slade |
| 7,654,418 | B2 * | 2/2010 | Law ................... B05B 11/3001 |
| | | | 222/259 |
| 7,659,398 | B2 | 2/2010 | Naddaka et al. |
| 7,874,467 | B2 | 1/2011 | Pardes et al. |
| 7,902,215 | B2 | 3/2011 | Statham et al. |
| 8,962,649 | B2 * | 2/2015 | Hutchings .............. A61P 17/00 |
| | | | 514/293 |
| 9,072,876 | B2 * | 7/2015 | Nordsiek ............. A61K 9/0031 |
| 9,642,998 | B2 * | 5/2017 | Nordsiek ............. A61K 9/0034 |
| 2005/0054991 | A1 | 3/2005 | Tobyn et al. |
| 2005/0189379 | A1 | 9/2005 | Py |
| 2007/0264317 | A1 | 11/2007 | Yosha et al. |
| 2008/0142112 | A1 | 6/2008 | Py et al. |
| 2009/0236374 | A1 | 9/2009 | Pardes et al. |

FOREIGN PATENT DOCUMENTS

| JP | 2002-165866 A | 6/2002 |
| WO | 2006/003481 | 1/2006 |
| WO | 2008/010963 | 1/2008 |
| WO | 2009/033053 | 3/2009 |
| WO | 2010/118458 A1 | 10/2010 |

OTHER PUBLICATIONS

Lebwohl et al., "Imiquimod 5% cream for the treatment of actinic keratosis: Results from two phase III, randomized, double-blind, parallel group, vehicle-controlled trials", 2004, J. Am. Acad. Dermatol., 50(5), pp. 714-721. (Year: 2004).*

Geisse et al., "Imiquimod 5% cream for the treatment of superficial basal cell carcinoma: Results from two phase III, randomized, vehicle-controlled studies", 2004, J. Am. Acad. Dermatol., 50(5), pp. 722-733. (Year: 2004).*

Swanson et al., "Imiquimod 2.5% and 3.75% for the treatment of actinic keratoses: Results of two placebo-controlled studies of daily application to the face and balding scalp for two 2-week cycles", 2010, J. Am. Acad. Dermatol., 62(4), pp. 582-590. (Year: 210).*

Cerner Multum, Inc.—Drug Information Online: Drugs.com. Nov. 5, 2007. "Aldara Consumer Information" [online] [retrieved on Jun. 3, 2010] Retrieved from the internet: URL: http://www.drugs.com/aldara.html?printable=1; Whole Document.

(Continued)

*Primary Examiner* — My-Chau T. Tran
(74) *Attorney, Agent, or Firm* — Kilpatrick Townsend & Stockton LLP

(57) ABSTRACT

A multidose package containing an imiquimod formulation suitable for treating topical conditions includes: a) a dispensing aperture for dispensing the formulation from the package; b) a reservoir containing sufficient formulation to provide two or more doses; c) a metered dosage element for measuring a predetermined dose of the formulation, the element including an inlet from the reservoir and an outlet to the dispensing aperture; and d) an actuating element operating the dosage element so the predetermined dose is delivered to the dispensing aperture; wherein the dose is dispensed without microbial or other contamination or degradation of the formulation in reservoir. A corresponding course of treatment for various maladies includes providing a multidose package containing an imiquimod formulation suitable for the treatment. A corresponding method of treatment of diseases with multiple doses of an imiquimod formulation includes multiple doses provided by a multidose package.

17 Claims, No Drawings

(56) References Cited

OTHER PUBLICATIONS

EPG Online—A service from EPG Health Media. Mar. 17, 2009. "Aldara 5 Cream" [online] [retrieved on Jun. 4, 2010] Retrieved from the internet: URL: http://www.epgonline.org/viewdrug.cfm/drugId/DR000599/language/LG0001/drugName/Aldara-5-Cream; Whole Document.

* cited by examiner

MULTIDOSE PACKAGE, COURSE AND METHOD OF TREATMENT FOR DELIVERING PREDETERMINED MULTIPLE DOSES OF A PHARMACEUTICAL

CROSS-REFERENCES TO RELATED APPLICATIONS

This application is a continuation of application Ser. No. 14/629,176, filed Feb. 23, 2015, which is a divisional of application Ser. No. 13/262,782, filed Dec. 30, 2011, which issued on Feb. 24, 2015 as U.S. Pat. No. 8,962,649, which is a 371 of International Application No. PCT/AU2010/000372, filed Apr. 1, 2010, which claims priority to Australian Application No. 2009901410, filed Apr. 1, 2009, the disclosures of which are each hereby incorporated by reference in their entirety for all purposes.

FIELD OF THE INVENTION

The present invention provides a multidose package for dispensing predetermined amounts of an imiquimod formulation suitable for treatment of topical conditions such as actinic keratosis, superficial basal cell carcinoma and external genital warts. A course of treatment and method of treatment are also provided.

BACKGROUND OF THE INVENTION

The compound imiquimod, [3-(2-methylpropyl)-3,5,8-triazatricyclo[7.4.0.02,6]trideca-1(9),2(6),4,7,10,12-hexaen-7-amine] is incorporated in a topical cream formulation for the treatment of skin lesions associated with actinic keratosis, basal cell carcinoma and anogenital warts.

Due to reactions in the formulation between some of the excipients and the preservatives, the formulation does not consistently comply with the British Pharmacopoeia preservative efficacy test. Because of this, therapeutic regulatory bodies limit the sale of the formulation to single-dose sachets in all countries where compliance with the British Pharmacopoeia test is mandatory. These formulations are presently sold in sets of six or 12 single-dose laminated sachets in Australia and other countries. The sachets comprise 250 mg of 5% w/w imiquimod cream.

The area and location of the lesions treated by the formulation vary according to the condition and its severity. This makes correct dosing of the cream difficult. For example, actinic keratosis (also known as solar keratosis) generally appears on areas of the body exposed to excessive sunlight such as the head, neck and the back of the hands. In severe cases there may be many lesions spread over a comparatively large area such as the entire scalp and forehead. Similarly basal cell carcinomas (BCC) may occur at various locations on the body whereas genital warts occur around the genital or anogenital region. Due to potential side effects of the cream, patients are warned to confine the treatment area to no larger than 20 cm$^2$. With conditions such as actinic keratosis where lesions may be spread over a relatively large part of the body, patients may be tempted to apply too much of the formulation. In contrast, in the case of small or less numerous lesions such as genital warts, the patient may apply too little of the formulation.

In addition to the above dosage difficulties, further difficulties arise because patients presently use a sachet more than once despite the manufacturer's warning not to re-use a sachet. The open sachet must be refrigerated to prevent microbial growth in case the remaining contents have been contaminated during use. As will be appreciated, contamination is a risk because some patients may not practice good hygiene. Depending on where and how the patient applies cream, this may increase the likelihood of contamination. Exposure to air may also adversely affect the cream. Further, access to refrigeration may be an issue where a patient is travelling or away from home. It may be embarrassing for a patient to have to ask a host to refrigerate a sachet, particularly for someone who is treating genital warts.

Statements made above about the prior art should not be taken to mean that the prior art discussed is part of the common general knowledge in the field, whether in Australia or elsewhere.

The present invention addresses at least some of the difficulties associated with currently available imiquimod creams in the treatment of the conditions discussed above.

BRIEF SUMMARY OF THE INVENTION

Accordingly, the present invention provides a multidose package containing an imiquimod formulation suitable for treating topical conditions such as actinic keratosis, superficial basal cell carcinoma and external genital warts, said package comprising: a) a dispensing aperture for dispensing the formulation from the package; b) a reservoir containing a sufficient amount of said formulation to provide two or more doses; c) a metered dosage means for measuring a predetermined dose of said formulation, said means comprising an inlet from said reservoir and an outlet to said dispensing aperture; and d) an actuating means for operating said dosage means such that the predetermined dose is delivered to said dispensing aperture; wherein said dose is dispensed without microbial or other contamination or degradation of the formulation in reservoir.

The present invention also provides a course of treatment of actinic keratosis, superficial basal cell carcinoma or external genital warts comprising provision of a multidose package containing an imiquimod formulation suitable for said treatment, the package comprising a dispensing aperture for dispensing the formulation from the package; a reservoir containing a sufficient amount of said formulation to provide the required number of doses for the course of treatment; a metered dosage means for measuring a predetermined dose of said formulation, said means comprising an inlet from said reservoir and an outlet to said dispensing aperture; and an actuating means for operating said dosage means such that the predetermined dose is delivered to said dispensing aperture; wherein said dose is dispensed without microbial or other contamination or degradation of the formulation in reservoir.

The present invention further provides a method of treatment of actinic keratosis, superficial basal cell carcinoma or external to genital warts with multiple doses of an imiquimod formulation characterised in that the multiple doses are provided by a multidose package said package comprising: a dispensing aperture for dispensing the formulation from the package; a reservoir containing a sufficient amount of said formulation to provide two or more doses; a metered dosage means for measuring a predetermined dose of said formulation, said means comprising an inlet from said reservoir and an outlet to said dispensing aperture; and an actuating means operating said dosage means such that the predetermined dose is delivered to said dispensing aperture; wherein said dose is dispensed without microbial or other contamination or degradation of the formulation in reservoir.

The present invention also extends to a method of providing a multidose package containing an imiquimod formulation suitable for treating topical conditions such as actinic keratosis, superficial basal cell carcinoma and external genital warts, said package comprising: a) a dispensing aperture for dispensing the formulation from the package; b) a reservoir for said formulation; c) a metered dosage means for measuring a predetermined dose of said formulation, said means comprising an inlet from said reservoir and an outlet to said dispensing aperture; and d) an actuating means for operating said dosage means such that the predetermined dose is delivered to said dispensing aperture; wherein said dose is dispensed without microbial or other contamination or degradation of the formulation in reservoir; said method comprising filling said reservoir with a sufficient amount of said formulation to provide two or more doses.

DETAILED DESCRIPTION

The term "multidose package" refers to a package capable of providing two or more doses. The package may be in the form of a container, bottle, tube, bag or other configuration suitable for pharmaceutical use.

The term "imiquimod formulation" refers to a formulation containing the compound imidazoquinoline amine 1-(2-methylpropyl)-1H-imidazo [4, 5-c] quinolin-4-amine as the active ingredient or at least one of the active ingredients. The synthesis of the compound is described in U.S. Pat. No. 4,689,338 at Example 99. The formulation may contain the compound in any pharmaceutically acceptable form, including any salt, isomer, solvate, polymorph, including enantiomers as well as mixtures of the enantiomers. The formulation may be in the form of a cream, a liquid, foam, a gel, an ointment or other suitable form.

The amount of imiquimod present in the formulation in the package will be an amount effective to treat the conditions mentioned. The total amount of imiquimod may be at least between about 0.1% and 10% by weight, based on the total weight of the composition. Unless otherwise indicated, all percentages provided herein are weight/weight with respect to the total weight of the composition. The formulation may include imiquimod at a concentration of 1%, 3%, 5%, or 6%. Preferably the amount will be about 5% imiquimod w/w.

The formulation may include one or more additional excipients such as, for example, a fatty acid, a thickener, an emulsifier, a solubilizing agent, an emollient, or a humectant.

The term "fatty acid" means a carboxylic acid, either saturated or unsaturated having 6 to 28 carbon atoms, such as, for example, from 10 to 22 carbon atoms. Fatty acids suitable for use in the formulations described herein include those that may aid in solubilizing imiquimod. Suitable fatty acids include, for example, isostearic acid, oleic acid, myristic acid, palmitic acid, palmitoleic acid, margaric acid, stearic acid, linoleic acid, linolenic acid, or mixtures thereof.

An amount of fatty acid sufficient to solubilize imiquimod is at least 0.05% by weight, at least 1.0% by weight, at least 3.0% by weight, at least 5.0%, at least 10%, at least 15%, or at least 25%, based on the total weight of the formulation and is at most 40% by weight, at most 30% by weight, at most 15% by weight, or at most 10% by weight, based on the total weight of the formulation.

The formulation may further include an emulsifier such as non-ionic surfactants polysorbate 60, sorbitan monostearate, polyglyceryl-4 oleate, polyoxyethylene (4) lauryl ether, poloxamers, and sorbitan trioleate present in an amount of 0.1% to 10% by weight of total formulation weight, for example, from 0.5% to 5.0% by weight, and from 0.75% to 4.0% by weight.

The formulation may also include viscosity-enhancing agents. Examples of suitable viscosity enhancing agents include long chain alcohols, for example, cetyl alcohol, stearyl alcohol, cetearyl alcohol; cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. In certain embodiments, the viscosity enhancing agent is xanthan gum. The amount of the viscosity enhancing agent, when used, is at least 0.1% by weight, at least 0.2% by weight, at least 0.5% by weight, at least 0.6% by weight, at least 0.7% by weight, at least 0.9% by weight, or at least 1.0% by weight, based on the total weight of the formulation.

The formulation may also include at least one emollient. Examples of suitable emollients include long chain alcohols, for example, cetyl alcohol, stearyl alcohol, cetearyl alcohol; fatty acid esters, for example, isopropyl mysristate, isopropyl palmitate, diisopropyl dimer dilinoleate; medium-chain (e.g., 8 to 14 carbon atoms) triglycerides, for example, caprylic/capric triglyceride; cetyl esters; hydrocarbons of 8 or more carbon atoms, for example, light mineral oil, white petrolatum; and waxes, for example, beeswax. Various combinations of such emollients can be used if desired. The emollient may be chosen from cetyl alcohol, stearyl alcohol, petrolatum, and mixtures thereof. The amount of the emollient is at least 1.0% by weight, at least 3.0% by weight, at least 5.0% by weight, or at least 10% by weight, based on the total weight of the formulation. In certain embodiments, the amount of emollient is at most 30% by weight, at most 15% by weight, or at most 10% by weight, based on the total weight of the formulation.

The formulation may be an oil-in-water emulsion. The water used in these formulations is typically purified water.

The formulation may also include additional pharmaceutically acceptable excipients such as humectants, such as for example, glycerin; chelating agents, such as for example, ethylenediaminetetraacetic acid; and pH adjusting agents, such as for example, potassium hydroxide or sodium hydroxide.

The multidose package may be a commercially available standard package. Generally the package will be in the form of a container comprising a dispensing aperture for dispensing the formulation connected to a metered dosage means in the form of a chamber able to accommodate the required volume of formulation for a single dose. The dispensing aperture may be in the form of a tube, an orifice, an outlet port, nozzle or the like. The chamber of the metered dosage means is of suitable volume to accommodate a single dose of the formulation which is admitted to the chamber via an inlet from the reservoir. A volume of about 80 mg of a 5% w/w imiquimod formulation is preferred. The chamber is connected via an inlet comprising a one way valve to the reservoir. The one way valve isolates the reservoir contents and prevents any back-flow of formulation into the reservoir once a volume of formulation enters the chamber. Thus microbial or other contamination or degradation including oxidation of the formulation in the reservoir is prevented. Preferably the metered dosage means is in the form of a positive displacement pump such as an airless pump and is operated by an actuator associated with the outlet port.

Preferably the airless pump has a body made as HD polyethylene, a piston made of LD polyethylene, an outlet port or stem of polypropylene and an inlet port or dip tube of polypropylene.

The package reservoir is any suitable container or receptacle for housing the required volume of formulation for the number of doses. Preferably the reservoir is made of polypropylene.

The multidose package may be a pump pack such as those supplied by Rexam Dispensing Systems™-airless dosing systems or Sunrise Pumps™-airless dispensers. Preferably the pump pack is the Rexam™ 2.05 ml Sof' Airless™.

Thus it can be seen from the above that the multi dose package of imiquimod of the invention is easy for the patient to carry and store, is adapted to suit different durations of treatment by providing a suitable amount of formulation in the reservoir and avoids the need for refrigeration of the formulation. Thus the multidose package of the invention provides patients with a much easier and more convenient way of treating the conditions of actinic keratosis, basal cell carcinoma and genital warts.

EXAMPLES

The following examples are offered to illustrate, but not to limit the claimed invention.

Example 1: Suitable Multidose Package

Various candidate containers from pharmaceutical container manufacturers are selected which have a metered dosage means able to deliver a predetermined dose of about 80 mg of imiquimod cream. The reservoir is filled with cream and the containers are tested to determine whether cream is retained in the nozzle past the one way valve after actuation of the pump. Cream retained in the nozzle could become contaminated therefore it is important that there is no cream retention. This is determined by visual examination and more accurately by weighing the pumps before and after dispensing. Only those containers in which there is no retention of cream in the nozzle are selected for further study.

Example 2: Initial Contamination Studies

Packs to be tested are filled with a bacterial growth medium, sealed and immersed in a bacterial dispersion and subjected to suitable conditions to allow bacterial growth. Presence of bacteria, if any, in the growth medium as a result of penetration into the packs is determined by standard microbiological assay.

Example 3: Simulated in Use" Test to Showing No Contamination During Multiple Use Description:
An "in use" test is used to determine that the formulation in the reservoir is not contaminated during multiple uses over a specified period such as one-month. After multiple doses of cream have been dispensed, the container is opened under aseptic conditions and tested for microbial contamination according to the British Pharmacopoeia Test for Microbial Contamination. Standard limits are applied. The test is also carried out on filled, untouched containers (i.e., containers that have not been used) to show that the cream is not contaminated prior to use.

Method
Each Rexam™ 2.05 mL Sof' Airless™ pump pack was aseptically filled with Aldara™ cream.

Filled pump packs under test were then exposed to multi-use by applying limited number of firing regimes on 5 different days. The filled pumps were stored for the storage and use life of the product (28 days, 25° C.). The microbial contamination of the remaining cream in the pump was measured by plating pouring method with TSA and SDA. TSA plates were incubated at 37° C. and SDA at 25° C. for 7 days. Negative controls were subjected to the same condition as sample containers without firing.

Each test regime was tested in quadruplicate pumps where two pumps were tested for bacteria and other two pumps were tested for yeast and mould.

Results:
Table 1 shows the absence of microbial growth from creams of the test pumps.

Table 2 shows the microbial assay of creams of the control pumps.

Table 3 indicates the weight of cream extract from each pump.

Bacterial contamination was not detected in any test products as well as the controls.

TABLE 1

Contamination organisms after cream exposed to different firing regime

| Firing day | Tests | TSA | SDA |
| --- | --- | --- | --- |
| 1 | TA01, TA02, TA03, TA04 | 0/2 | 0/2 |
| 2 | TA07, TA08, TA00, TA10 | 0/2 | 0/2 |
| 3 | TA13, TA14, TA15, TA16, | 0/2 | 0/2 |

TABLE 2

Contamination organisms of the controls

| Firing day | Tests | TSA | SDA |
| --- | --- | --- | --- |
| 1 | CA01, CA02 | 0/1 | 0/1 |
| 2 | CA07, CA08 | 0/1 | 0/1 |
| 3 | CA13, CA14 | 0/1 | 0/1 |

TABLE 3

Weight of Aldara ™ Cream from each pump and corresponding volume of Neutraliser added per sample.

| Sample Description | Net Weight per pump (g) | Volume of Neutralizer added (ml) |
| --- | --- | --- |
| TA01 | 1.2179 | 12.2 |
| TA02 | 1.2319 | 12.3 |
| TA03 | 1.2814 | 12.8 |
| TA04 | 1.2740 | 12.7 |
| CA01 | 1.6518 | 16.5 |
| CA02 | 1.5997 | 16.0 |
| TA07 | 1.1582 | 11.6 |
| TA08 | 0.8936 | 9.0 |
| TA09 | 1.1035 | 11.0 |
| TA10 | 0.9373 | 9.4 |
| CA07 | 1.7640 | 17.6 |
| CA08 | 1.7308 | 17.3 |
| TA13 | 0.4279 | 4.3 |
| TA15 | 0.4823 | 4.8 |
| TA16 | 0.8398 | 8.4 |
| CA13 | 1.6731 | 16.7 |
| CA14 | 1.2687 | 12.7 |

Example 4: Compatibility of Multi-Dose Container Components and Formulation

Once a candidate package is identified, stability trials are carried out to determine compatibility of the formulation with the container components. Testing is carried out on the formulation packed in the selected containers and stored under a number of controlled conditions (e.g., 40° C./75% RH and 25° C./60% RH) for a specified time up to the expiry date of the product. Tests will include determination of imiquimod content, preservative content, impurity content, appearance, microscopic examination, pH levels and visual container assessment against set standards.

Example 5: Stability of Formulation in Multi-Dose Container

Two batches of Aldara cream were dispensed into Rexam™ 2.05 mL Sof' Airless™ containers. The batches had been previously tested to determine the amount of preservatives (methyl hydroxybenzoate (MHB), propyl hydroxybenzoate (PHB) benzyl alcohol) and imiquimod, at the beginning of the study in Table 4 below.

Finished Product Expiry Specifications- to be applied at all test points:

| | |
|---|---|
| Imiquimod | 4.50-5.50% w/w |
| Methyl Hydroxy Benzoate (MHB) | 0.18-.0.22% w/w |
| Propyl Hydroxy Benzoate (PHB) | 0.018-0.022% w/w |
| Benzyl Alcohol | 1.00-2.10% w/w |
| 4-Hydroxyimiquimod (Impurity) | NMT 0.3% w/w (relative to label claim of imiquimod) |

TABLE 4

Aldara Cream 5% w/w Imiquimod

| Initial Data Batch no. | % w/w Benzyl Alcohol | % w/w MHB | % w/w PHB | % w/w Imiquimod |
|---|---|---|---|---|
| 063/GLB038A | 1.94 | 0.200 | 0.020 | 4.98 |
| 064/GLB052A | 1.95 | 0.200 | 0.020 | 5.00 |

The batches were stored under various conditions and then analyzed at 2 months, 4 months, 5.5 months and 13 months as shown in Tables 5 to 7 below. The presence of the contaminant 4-OH-R837 was also tested. NOTE: 4-OH-R837 is an Imiquimod impurity.

TABLE 5

Aldara Cream 5% w/w Pump 40° C./75% RH 2 months

| Batch no. | % w/w Benzyl Alcohol | % w/w MHB | % w/w PHB | % w/w Imiquimod | % of R837 4-OH-R837 |
|---|---|---|---|---|---|
| 063/GLB038A | 1.64 | 0.205 | 0.020 | 5.06 | <0.01 |
| 064/GLB052A | NT | NT | NT | NT | NT |

NT = not tested

TABLE 6

Aldara Cream 5% w/w Imiquimod 40° C./75% RH 4 months

| Batch no. | % w/w Benzyl Alcohol | % w/w MHB | % w/w PHB | % w/w Imiquimod | % of R837 4-OH-R837 |
|---|---|---|---|---|---|
| 063/GLB038A | 1.44 | 0.201 | 0.020 | 5.07 | <0.01 |
| 064/GLB052A | 1.44 | 0.200 | 0.020 | 5.04 | <0.01 |

TABLE 7

Aldara Cream 5% w/w Imiquimod 5 C./60% RH and 40° C./75% RH 5.5 months

| Batch no. | % w/w Benzyl Alcohol | % w/w MHB | % w/w PHB | % w/w Imiquimod | % of R837 4-OH-R837 |
|---|---|---|---|---|---|
| 063/GLB038A | | | | | |
| 25° C./60% RH | 1.66 | 0.198 | 0.020 | 5.02 | <0.01 |
| 40° C./75% RH | 1.33 | 0.206 | 0.022 | 5.19 | <0.01 |
| 064/GLB052A | | | | | |
| 25° C./60% RH | 1.76 | 0.198 | 0.020 | 5.02 | <0.01 |
| 40° C./75% RH | 1.34 | 0.204 | 0.022 | 5.18 | <0.01 |

TABLE 8

Aldara Cream 5% w/w Imiquimod 25 C./60% RH and 40° C./75% RH 13 months

| Batch no. | % w/w Benzyl Alcohol | % w/w MHB | % w/w PHB | % w/w Imiquimod | % of R837 4-OH-R837 |
|---|---|---|---|---|---|
| 063/GLB038A | | | | | |
| 25° C./60% RH | 1.52 | 0.21 | 0.02 | 5.26 | <0.01 |
| 40° C./75% RH | 0.99 | 0.21 | 0.02 | 5.30 | <0.01 |
| 064/GLB052A | | | | | |
| 25° C./60% RH | 1.53 | 0.21 | 0.02 | 5.15 | <0.01 |
| 40° C./75% RH | 0.98 | 0.21 | 0.02 | 5.28 | <0.01 |

Data up to and including 13 months indicates good stability at both 25 C/60% RH and 40 C/75% RH for Imiquimod, MHB and PHB. The Impurity (4 Hydroxy Imipquimod) is below detection limits. Benzyl alcohol levels have dropped at 40 C/75% RH to just below the lower specification limit and will continue to be stable at 25 C/60% RH which is the marketed product storage temperature.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treatment of actinic keratosis, superficial basal cell carcinoma or external genital warts in a patient in need thereof, said method comprising administering to said patient multiple doses of an imiquimod formulation, wherein said multiple doses are provided by a multidose package, said package comprising:
   a) a dispensing aperture for dispensing the formulation from the package;
   b) a reservoir containing a sufficient amount of said formulation to provide two or more doses;
   c) a metered dosage means for measuring a predetermined dose of said formulation, said means comprising an inlet from said reservoir and an outlet to said dispensing aperture, wherein the metered dosage means is in the form of a positive displacement pump and is operated by an actuator associated with the outlet; and
   d) an actuating means operating said dosage means such that the predetermined dose is delivered to said dispensing aperture; wherein said dose is dispensed without microbial or other contamination or degradation of the formulation in reservoir.

2. The method of treatment of claim 1, wherein the inlet comprises a one way valve to the reservoir.

3. The method of treatment of claim 2, wherein the one way valve isolates the reservoir contents and prevents any back-flow of air and/or formulation into the reservoir once a volume of formulation enters the metered dosage means.

4. The method of treatment of claim 1, wherein an airless pump is associated with said metered dosage means.

5. The method of treatment of claim 4, wherein the airless pump has a body made of HD polyethylene, a piston made of LD polyethylene, an outlet port or stem of polypropylene and an inlet port or dip tube of polypropylene.

6. The method of treatment of claim 1, wherein the imiquimod is present in the formulation in an amount of 0.1 to 10% w/w.

7. The method of treatment of claim 1, wherein the imiquimod is present in the formulation in an amount of 5% w/w.

8. The method of treatment of claim 1, wherein the method of treatment is for actinic keratosis.

9. The method of treatment of claim 8, wherein the package has a volume of formulation in the reservoir suitable for treatment for 2 weeks, 3 weeks or 6 weeks.

10. The method of treatment of claim 1, wherein the method of treatment is for basal cell carcinoma.

11. The method of treatment of claim 10, wherein the package has a volume of formulation in the reservoir suitable for treatment for 2 weeks, 4 weeks, 8 weeks or 16 weeks.

12. The method of treatment of claim 1, wherein the method of treatment is for genital warts.

13. The method of treatment of claim 12, wherein the package has a volume of formulation in the reservoir suitable for treatment for 2 weeks, 4 weeks, 8 weeks or 16 weeks.

14. The method of treatment of claim 6, wherein the package has a volume of formulation in the reservoir suitable for 6, 12 or 24 doses.

15. The method of treatment of claim 6, wherein the predetermined dose is about 80 mg of formulation.

16. A method for treating external genital warts in a patient in need thereof, said method comprising administering to said patient multiple doses of an imiquimod formulation, wherein said multiple doses are provided by a multidose package, said package comprising: a dispensing aperture for dispensing the formulation from the package; a reservoir containing a sufficient amount of said formulation to provide the required number of dosages for the course of treatment; a metered dosage means for measuring a predetermined dose of said formulation, said means comprising an inlet from said reservoir and an outlet to said dispensing aperture, wherein the metered dosage means is in the form of a positive displacement pump and is operated by an actuator associated with the outlet; and an actuating means for operating said dosage means such that the predetermined dose is delivered to said dispensing aperture; wherein said dose is dispensed without microbial or other contamination or degradation of the formulation in reservoir and wherein the imiquimod is present in the formulation in an amount of 0.1 to 10% w/w.

17. A method of providing a multidose package containing an imiquimod formulation suitable for treating a topical condition selected from the group consisting of actinic keratosis, superficial basal cell carcinoma and external genital warts, said package comprising: a) a dispensing aperture for dispensing the formulation from the package; b) a reservoir for said formulation; c) a metered dosage means for measuring a predetermined dose of said formulation, said means comprising an inlet from said reservoir and an outlet to said dispensing aperture, wherein the metered dosage means is in the form of a positive displacement pump and is operated by an actuator associated with the outlet; and d) an actuating means for operating said dosage means such that the predetermined dose is delivered to said dispensing aperture; wherein said dose is dispensed without microbial or other contamination or degradation of the formulation in reservoir; said method comprising filling said reservoir with a sufficient amount of said formulation to provide treatment for 2 weeks, 4 weeks, 8 weeks or 16 weeks.

* * * * *